(12) United States Patent
Roe et al.

(10) Patent No.: US 8,182,576 B2
(45) Date of Patent: *May 22, 2012

(54) APPARATUS AND METHOD FOR BIOGAS PURIFICATION

(75) Inventors: Kevin L. Roe, Unity, WI (US); David J. Mandli, Mosinee, WI (US); Amanda M. Neuhalfen, Wausau, WI (US)

(73) Assignee: A&B Process Systems Corporation, Stratford, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/214,944

(22) Filed: Aug. 22, 2011

(65) Prior Publication Data

US 2012/0000357 A1    Jan. 5, 2012

Related U.S. Application Data

(63) Continuation of application No. 12/190,731, filed on Aug. 13, 2008, now Pat. No. 8,007,567.

(51) Int. Cl.
*B01D 19/00* (2006.01)
*B01D 36/04* (2006.01)
*B01D 37/04* (2006.01)
*B01D 61/58* (2006.01)

(52) U.S. Cl. ............. 95/12; 95/42; 95/46; 95/47; 95/54; 95/179; 96/6; 96/219; 96/240; 96/242; 96/252

(58) Field of Classification Search .............. 95/8, 12, 95/42, 46, 47, 54, 159, 178, 179, 191, 193; 96/6, 219, 240, 242, 252, 417

See application file for complete search history.

(56) References Cited

U.S. PATENT DOCUMENTS

| | | | | |
|---|---|---|---|---|
| 2,274,094 A | * | 2/1942 | Rupp | 95/42 |
| 3,662,017 A | * | 5/1972 | Woerner et al. | 95/42 |
| 4,070,231 A | * | 1/1978 | Alleman | 159/47.1 |
| 4,078,390 A | * | 3/1978 | Duvall | 95/15 |
| 4,132,535 A | * | 1/1979 | Rivers et al. | 95/42 |
| 4,138,230 A | * | 2/1979 | Thompson | 95/169 |
| 4,409,102 A | * | 10/1983 | Tanner | 210/603 |
| 4,597,777 A | * | 7/1986 | Graham | 95/51 |
| 4,627,922 A | * | 12/1986 | Viator et al. | 210/704 |
| 4,638,852 A | * | 1/1987 | Basseen et al. | 165/47 |
| 4,761,968 A | * | 8/1988 | Basseen et al. | 62/271 |
| 5,107,919 A | * | 4/1992 | Basseen et al. | 165/47 |

(Continued)

FOREIGN PATENT DOCUMENTS

EP    0180670 A1 *  5/1986

(Continued)

*Primary Examiner* — Richard L Chiesa
(74) *Attorney, Agent, or Firm* — Boyle Fredrickson, S.C.

(57) ABSTRACT

The present invention is a biogas processing system having a compressor having a biogas input and output, a pump having a water input and output, a scrubber tower having a mixing chamber connected to a biogas input, a water pump input, a water output, and a processed biogas output, and a filtration member connected to the water output to remove contaminants from the water exiting the first scrubber tower. The system also includes devices for heating and cooling the recycled flow of water to enhance the ability of the water to absorb contaminants from the biogas and the ability of a stripper to remove absorbed contaminants from the water in a closed loop water system, and a controller for closely controlling the operating parameters of the system to achieve safe and optimal operation of the system.

18 Claims, 1 Drawing Sheet

U.S. PATENT DOCUMENTS

| | | | | |
|---|---|---|---|---|
| 5,207,895 A | * | 5/1993 | Basseen et al. | 210/95 |
| 5,306,331 A | * | 4/1994 | Auvil et al. | 95/42 |
| 5,611,840 A | * | 3/1997 | Kraus et al. | 95/41 |
| 5,871,563 A | * | 2/1999 | Roth et al. | 95/42 |
| 6,986,802 B2 | * | 1/2006 | Colling et al. | 95/46 |
| 8,007,567 B2 | * | 8/2011 | Roe et al. | 95/12 |
| 2006/0213370 A1 | * | 9/2006 | Leonard et al. | 96/243 |
| 2007/0224669 A1 | * | 9/2007 | Jewell | 435/167 |
| 2008/0134754 A1 | * | 6/2008 | Funk | 73/23.41 |
| 2009/0013868 A1 | * | 1/2009 | Darde et al. | 95/42 |
| 2010/0037772 A1 | * | 2/2010 | Roe et al. | 95/42 |

FOREIGN PATENT DOCUMENTS

| | | |
|---|---|---|
| EP | 1733781 A1 * | 12/2006 |
| JP | 62-144729 A * | 6/1987 |

* cited by examiner

APPARATUS AND METHOD FOR BIOGAS PURIFICATION

CROSS-REFERENCE TO RELATED APPLICATION

This application is a continuation of U.S. patent application Ser. No. 12/190,731, filed Aug. 13, 2008, issued as U.S. Pat. No. 8,007,567, on Aug. 30, 2011, the entirety of which is expressly incorporated herein.

FIELD OF THE INVENTION

The present invention relates to systems and methods for the purification of biogas, and in particular to the production of high purity natural gas from a biogas source for use as an energy source.

BACKGROUND OF THE INVENTION

Machines of all sorts rely upon refined petroleum products, such as gas and motor oil, in order to operate. The increasing number of machines built and sold each year ensures that the amount of fuel supplied in a given period of time will eventually not be able to support all the vehicles in operation. Additionally, there are significant and wide-spread concerns about the environmental aspects of fossil fuels attributed significantly to global warming. Fossil fuels are a non-renewable resource having only a finite supply which has sparked concern about energy shortages or a world-wide energy crisis if fossil fuel production ceased or otherwise lagged behind demand. Therefore, alternative energy and fuel research is an important and competitive industry.

Natural gas is one of the cleanest burning fossil fuels, and millions of vehicles worldwide have been modified or built to run on it. In fact, the infrastructure to support the use of natural gas has been developed in some areas where its purer combustion properties are highly valued. Unfortunately, there are a number of drawbacks to using natural gas as a transportation fuel. First, natural gas is still a non-renewable resource. The finite supply of natural gas means the price fluctuates with production. In general, natural gas is not an economically competitive alternative for most consumers. Also, burning natural gas still contributes to global warming gases. Finally, the energy density at which combustion occurs is over one thousand times less than conventional liquid fuels. In order to overcome its low energy density, natural gas must be highly pressurized. High pressures must be combined with low temperatures in order to convert natural gas into a dense, easily transported liquid fuel.

Natural gas mainly consists of methane ($CH_4$), but, depending on the terrestrial origin of the gas, it can contain other trace gases such as hydrogen sulfide, hydrogen, propane, butane, etc. While natural gas is a non-renewable resource, methane is generated as a natural by-product of anaerobic fermentation or digestion, which is a ubiquitous environmental process essential for reducing organic matter in the natural environment. The main by-products of anaerobic digestion are methane, at generally one-half to two-thirds of the resulting gas, and carbon dioxide, along with trace levels of hydrogen sulfide, oxygen, nitrogen and water vapor. Almost all of the energy in the original biodegradable organic matter is contained in this renewable source of methane.

One alternative to the heavy reliance on fossil fuels involves purifying the gas that results from anaerobic digestion, also known as "biogas," in order to produce a pure, renewable methane stream. Typically, anaerobic digestion devices (i.e., anaerobic digestion that is not occurring in nature) are intended to convert organic material, also known as "biomass," from one form to another. For example, biomass can be placed in a silo for partial fermentation that converts the biomass to animal feed. Anaerobic digestion is also used to treat plant, animal and human waste. These waste materials can be converted into a fertilizing material. Yet, methane produced from anaerobic digestion would still need to be compressed to greater than 2000 pounds/inch$^2$ (2000 'psi') in order to approach the energy density of conventional liquid fuels. Even at 2000 psi, methane is a gas, and it would need to be purified, for some applications, before being used as a fuel. Known biogas purification and compression methods and apparatuses can not produce a cost-effective fuel. As such, methods and devices for producing biogas from anaerobic digestion have been rejected as viable alternatives for the production of fuel. A suitable process would provide a renewable fuel source while treating waste products that must otherwise be disposed of as well as being capable or using most sources of photosynthetically fixed biomass.

The fuel in biogas powered machines uses the same engine configuration as natural gas machines. The gas quality demands are strict. The raw biogas from a digester need to be upgraded in order to obtain biogas which: 1) has a higher calorific value in order to provide more energy output; 2) has a regular/constant gas quality to obtain safe operation of the machine utilizing the biogas as an energy source; 3) does not enhance corrosion due to high levels of hydrogen sulfide, ammonia, and water; 4) does not contain mechanically damaging particles, 5) does not give ice-clogging due to a high water content and 6) has a declared and assured quality. In practice, this means that carbon dioxide, hydrogen sulfide, ammonia, particles and water (and other trace components) have to be removed so that the product gas for vehicle fuel use has methane content above 95%. Different quality specifications for vehicle fuel use of biogas and natural gas are applied in different countries.

A number of biogas upgrading technologies have been developed for the treatment of different sources of biogas, such as natural gas, sewage gas, landfill gas, etc. At present, four different methods are used commercially for removal of carbon dioxide from biogas either to reach vehicle fuel standard or to reach natural gas quality for injection to the natural gas grid.

Primarily, water scrubbing is used to remove carbon dioxide but also hydrogen sulfide from biogas, since these gases are more soluble in water than methane. The absorption process is purely physical. Usually the biogas is pressurized and fed to the bottom of a packed column where water is fed to the top so the absorption process is operated counter-currently. The water which exits the column with absorbed carbon dioxide and/or hydrogen sulfide can be regenerated and re-circulated back to the absorption column. The regeneration is made by depressurizing or stripping with air in a similar column. Stripping with air is not recommended when high levels of hydrogen sulfide are handled since the water will soon be contaminated with elementary sulfur which causes operational problems. The most cost efficient method is not to re-circulate the water if cheap water can be used, for example, outlet water from a sewage treatment plant.

However, this purification process has a number of limitations, in particular, the inability to significantly remove the $O_2$ and/or the $N_2$ components of the biogas. The $O_2$ and $N_2$ present in the biogas can build up over time and negatively affect the purity of the natural gas, making unsuitable for introduction directly into a natural gas pipeline. In addition, the amount of water that is necessary to enable the stripping process to operate effectively is very high, which makes the utilization of suitable water-regeneration processes undesirable.

Therefore, there exists a need for a system for methane production using biogas produced as the result of anaerobic digestion or other similar processes that can sufficiently remove not only the primary contaminants from the biogas, such as carbon dioxide and hydrogen sulfide, but also more trace impurities, e.g., $O_2$, $N_2$, and moisture to produce a pipeline quality natural gas.

SUMMARY OF THE INVENTION

According to one object of the present invention, a biogas processing system includes a series of key functional elements which when sequentially combined and properly controlled will consistently purify raw biogas to meet or exceed F.E.R.C. specifications for commercial pipeline quality natural gas. The biogas processing system includes a means for removing water and/or hydrogen sulfide from biogas before the biogas enters a first compressor having a biogas input and a compressed biogas output, a first pump having a water input and a water output, and a first scrubber tower. The first scrubber tower includes a mixing chamber, a compressed gas input, a water input coupleable to the water output of the first pump, a water output, and a processed gas output. The mixing chamber is in communication with the compressed gas input, the compressed gas output, the water input and the water output. The biogas processing system also includes a second scrubber tower having a mixing chamber, a compressed gas input in communication with the output of the first scrubber tower, a water input, a water output, and a processed gas output. The biogas processing system further includes a flash tank having a water input coupled to the water output of the first scrubber, a water output, and a gas recirculation output. To remove unwanted oxygen from the process stream, the water used in the scrubber tower is passed through a recycling system that utilizes a flash tank, air degasification and a membrane filtration system to clean the water prior to reintroduction of the water into the scrubbers. In addition, suitable anion/cation bed technology can be employed to further clean the water, thereby prevent build up of these impurities in the biogas stream.

According to another aspect of the present invention, the temperature of the water exiting the scrubber tower(s) is modified prior to entering the recycling system in order to enhance the ability of the recycling system to remove those contaminants contained within the water exiting the scrubbers. This temperature change is effected by passing the water through a number of other components of the system to cool the process streams flowing through those components prior to being directed into the recycling system.

According to still another aspect of the present invention, the system and method further includes remotely monitoring the processing of biogas, and sending a command from a remote location to adjust at least one processing parameter and electrically executing the command. The remote sensing and communication systems allow for remote monitoring and remote control of the processing system, which can be advantageous because staffing is not necessarily available at all times at remote processing locations. In some examples, the system requires little or no on-site human supervision.

Numerous other aspects, features, and advantages of the present invention will be made apparent from the following detailed description taken together with the drawing FIGURE.

BRIEF DESCRIPTION OF THE DRAWING FIGURES

The drawing illustrates the best mode currently contemplated of practicing the present invention.

In the drawings:

The drawing FIGURE is a schematic illustration of a biogas purification system constructed according to the present invention.

DETAILED DESCRIPTION OF THE INVENTION

The following detailed description includes references to the accompanying drawing, which form a part of the detailed description. The drawing shows, by way of illustration, a specific embodiment in which the invention may be practiced. This embodiment, which is also referred to herein as an "example," is described in enough detail to enable those skilled in the art to practice the invention. The embodiment may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference.

Figure 1:
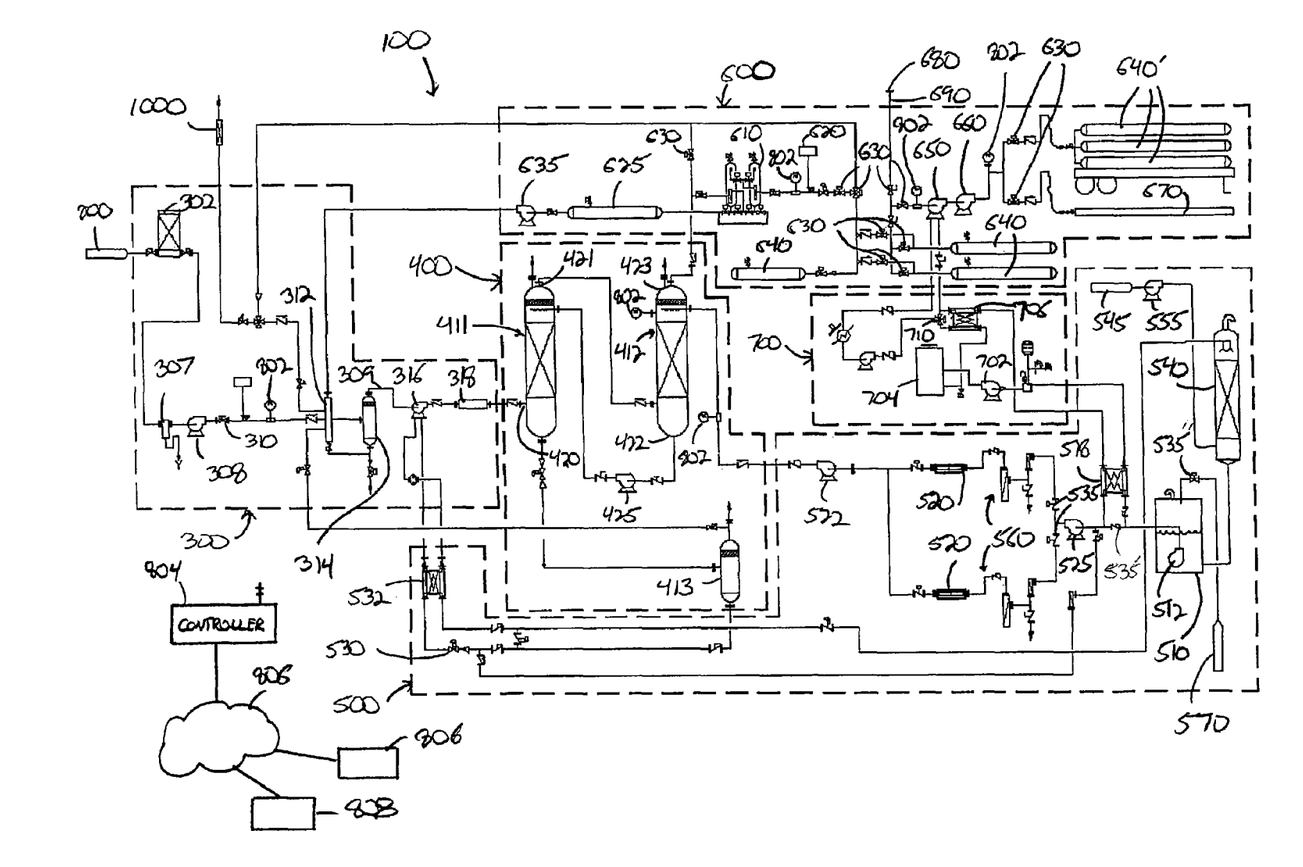

The drawing FIGURE is a schematic illustration of an example of a biogas processing system 100 that includes a biogas compression system 300, biogas scrubber system 400, water supply system 500, and analysis and final processing system 600. Water and biogas are processed through components of the biogas compression system 300, biogas scrubber system 400, water supply system 500, and analysis and final processing system 600 to process biogas into a more usable form, such as methane. In the system 100, each of the various components of the subsystems 300, 400, 500, 600 and 700 are connected by suitable members, such as piping, that conduct the material handled by the particular subsystem 300, 400, 500, 600 and 700 between the components of the subsystem 300, 400, 500, 600 and 700 at the required temperatures and pressures for proper operation of the subsystem 300, 400, 500, 600 and 700 in a manner as is known in the art.

In an exemplary embodiment, the system 100 includes one, and preferably multiple digesters 200 or other suitable sources of raw biogas that is supplied to the system 100. In some embodiments of the invention, the raw biogas is produced at a biogas site utilizing anaerobic digestion of organic materials, e.g., manure, e.g., human, hog, turkey, chicken and/or cattle manure. The organic materials may be located at a biogas site, e.g., a landfill or a farm. Raw biogas typically includes a mixture of carbon dioxide and methane with trace levels of hydrogen sulfide and water vapor, and more particularly containing 55%-75% of methane, 25%-40% carbon dioxide and other components, such as hydrogen sulfide, oxygen and nitrogen gases. The biogas from the digesters 200 is also saturated with water at a pressure of about 4-12 psig, with a volumetric flow range from the digesters 200 of approximately 5,000-50,000 standard cubic feet per hour.

The raw biogas is then directed via suitable conducting member, such as piping, to a biogas compression system 300, where the biogas is treated to remove the hydrogen sulfide and water, and to compress the biogas for further processing by the system 100.

The biogas compression system 300 includes a hydrogen sulfide cleaning system 302, a moisture knockout vessel 307, a first compressor 308, an accumulator 312, a pre-conditioner 314, a second compressor 316 and a cooler 318 that are each connected to one another by suitable piping 309 that also includes one or more valves 310 to control the flow of biogas between the components of the system 300.

Raw biogas is initially fed from the digesters 200 through the hydrogen sulfide cleaning system 302, which removes hydrogen sulfide from the biogas. Hydrogen sulfide is removed in the system 302 by any suitable process, such as by air/oxygen dosing to the digester biogas, and iron chloride dosing to the digester slurry, among others. However a preferred method for removal of at least a portion of the hydrogen sulfide in the system 302 is to pass the biogas through an iron sponge under proper conditions to oxidize the hydrogen sulfide. The reasons for the removal of the hydrogen sulfide are because the presence of sulfur gases, i.e., hydrogen sulfide, downstream will aggressively degrade metal equipment and sensors, and hydrogen sulfide is also a personnel hazard, even when present at very minor concentrations, which requires its removal from the biogas stream.

The biogas passes out of the hydrogen sulfide cleaning system 302 and is directed into the moisture separator 307. The moisture separator 307 reduces the moisture content of the biogas from the saturated moisture content present when exiting the digester 200 to less than about 1.4%. Any condensed moisture present downstream will create problems for system control as it interferes with gas flow and pressure measurements. If not removed, condensation also causes rapid failure of compressor lube oil filters and internal lubricated parts.

The biogas output from the moisture separator 307 enters the first compressor 308, which is powered by a motor (not shown) which can be an electric motor powered by a generator that is powered by a biogas-operable engine or a crude methane-operable engine (not shown). Using biogas or methane energy to power the motors allows the system to be self-contained.

After passing through the compressor 308, the biogas enters an accumulator 312 that combines the compressed biogas stream with recycled gas streams coming from a flash tank 413 and gas drier 610. The combined biogas stream is then directed from the accumulator 312 into a pre-conditioner 314. The pre-conditioner 314 serves to pre-cool accepted biogas to separate and remove condensed moisture.

From the pre-conditioner 314 the biogas stream is directed through the second compressor 316 and into the cooler 318. In the cooler 318 the biogas stream is thermally contacted with a cooling water stream to reduce the temperature of the biogas stream below about 70° F. for introduction into the scrubber system 400.

The compressed and cooled biogas is supplied to the biogas scrubber system 400. Biogas processing plants typically remove carbon dioxide from biogas through water absorption. Water absorption or "water scrubbing" techniques are predicated on the relative solubility of methane and carbon dioxide in water. Carbon dioxide is more soluble in water under pressure than at atmospheric pressure. Methane is mostly insoluble even at elevated pressures. Pressurizing a methane/carbon dioxide biogas mixture in the presence of water drives carbon dioxide into solution in the water but drives little methane into solution. The resulting processed biogas has an enriched methane content because some or all of the carbon dioxide has been processed out of the gas and into solution in the water. The optimum relative solubility difference for methane and carbon dioxide is in the range from one hundred fifty (150) to two hundred (200) pounds per square inch gauge (psig). The compressed operating pressure is a function of the temperature, carbon dioxide mole fraction in the gas, and the desired methane purity.

The scrubber system 400 is also connected to a water supply system 500 that pumps water into the scrubber system. The gas flows in counter-flow or cross-flow with the water. As the gas flows past the water, carbon dioxide is absorbed into the water. Some methane is typically also absorbed into the water. However, substantially less methane is absorbed into the water than carbon dioxide because of the difference in relative water solubility between methane and carbon dioxide. In an example, at about 200 psig, nearly all of the carbon dioxide in biogas is absorbed into water and about 5% of methane is absorbed, even though methane is the more prevalent component in biogas.

In the drawing, the biogas scrubbing system 400 includes first and second scrubber towers 411, 412 and a flash tank 413 each connected by suitable piping 414 and a number of valves 416, though different number of scrubbing towers can be employed as desired. Preferably, the scrubber towers 411 and 412 move biogas and water in counter-flow. For example, the scrubber towers 411 and 412 can include one or more internal vertical columns that contain Rashig rings, sieve plates, bubble cap or disk and donut gas/liquid contact devices. In another embodiment, the scrubber system 400 includes one or more cross-flow chambers in which water is passed in cross-flow over the biogas. The compressed biogas is introduced at or near the bottom 420 of tower 411. Water is introduced at or near the top 421 of the tower 411. As the water moves down the tower, biogas flows up the tower and exits near the top 421 of the tower 411. At least some of the carbon dioxide in the gas is absorbed into the water. The gas exiting the top of the tower 411 has a higher concentration of methane than the gas entering the bottom of the tower 411 because some of the carbon dioxide is removed from the gas. In the preferred embodiment shown in the drawing FIGURE, two sequential scrubber towers 411 and 412 are used. The gas exiting the top 421 of the first tower 411 is introduced into the bottom 422 of the second tower 412. Water enters at the top 423 of the second tower 412 and gas is introduced at the bottom 422 of the second tower 412. In the system 100 shown in the drawing FIGURE, the biogas flows in counter-current to the water, i.e., water exiting the bottom of the second tower enters a pump 425 and is delivered to the top of the first tower 411. In an alternative embodiment, water can be provided directly to each tower 411 and 412 instead of circulating through the towers 411 and 412. Supplying the water in counter-current to the gas makes more efficient use of the water. In addition, directly supplying fresh or de-gassed water provides more efficient or effective biogas scrubbing in certain situations, for example, when the water would become saturated with carbon dioxide in counter-current flow through the towers 411 and 412.

The carbon dioxide-laden water generated in the water scrubbing towers 411 and 412 is passed to a flash vessel or tank 413 operated at a lower pressure than the water scrubber towers 411 and 412 which pulls at least some of the methane out of the water. In particular, the water output from the scrubber towers 411 and 412 is at about one hundred fifty (150) to about two hundred (200) psig, and the flash tank is at about 25-100 psig. Because of the difference in solubility between methane and carbon dioxide, methane desorbs out of the water more quickly and easily than carbon dioxide. The reclaimed methane that is flashed out of the water in the flash tank 413 is then introduced back into the biogas stream at the accumulator 312.

The biogas stream that exits the scrubber system 400 through the top 423 of the tower 412 is a purified, processed or "cleaned" biogas which essentially comprises crude methane. This processed biogas is subsequently delivered to an analysis and final processing system 600. The analysis and final processing system 600 removes water vapor and trace contaminants from the processed gas, tests the composition of the gas, and compresses the gas for storage or transport via truck or pipeline.

Initially, the processed biogas is passed through a drier and purifier 610 that removes water vapor and trace contaminants remaining in the processed biogas. Air driers and purifiers are commercially available, for example, from Pioneer Air Systems. Driers and/or purifiers and related components are described in U.S. Pat. Nos. 4,761,968, 4,638,852, 4,499,033, 5,107,919 and 5,207,895, among others.

Downstream from the drier and purifier 610, the analysis and final processing system 600 includes gas analyzers 620 which sample the processed gas to determine its makeup. The parameters for the gas measured by the analyzers 620 can be calibrated to ensure the processed gas meets either FERC or DOT standards for compressed natural gas (CNG) or liquefied natural gas (LNG). The parameters for each of these standards are shown in Table 1:

TABLE 1

Natural Gas Standards

| Component or Property | Units of Measure | FERC Pipeline Spec | CNG Spec per DOT |
|---|---|---|---|
| Water vapor | Lbs per mmscf (million std cu ft) | Less than 6 | Less than 0.5 |
| Hydrogen sulfide | Grains per Ccf | Less than or equal to 0.25 | Less than or equal to 0.10 |
| Total sulfur | Grains per Ccf | Less than or equal to 20 | Less than 0.1 |
| Heating value | Btu per Cubic Foot | Greater than or equal to 950 | |
| Temperature | Degrees Fahrenheit | Less than or equal to 120 F. | |
| Oxygen | Percent by volume | Less than or equal to 0.2 | Less than 1.0 |
| Carbon dioxide | Percent by volume | Less than or equal to 2.0 | Less than 3.0 |
| Non-hydrocarbon gases | Percent by volume | | Less than 4.0 |

If the analyzers 620 determine that the processed gas is outside of one or more of these parameters, the analyzer 620 will cause the gas to be directed via valves 630 to either local flare 1000 for combustion, or to a storage tank 625 and compressor 635 for subsequent direction to the accumulator 312 for re-introduction into the scrubbing system 400 for further cleaning.

However, if the process gas has been sufficiently purified to meet the standards set in the analyzers 620, the gas is directed by the valve 630 to one or more tanks 640 or for use within the facility housing the system 100, or to mobile storage tanks 640' used to transport the gas to another location for use. For that portion of the processed gas directed to the storage tanks 640, the gas can be directed to third and fourth compressors 650 and 660 driven by a suitable motor (not shown) that is optionally coupled to a biogas or methane-operable combustion engine (not shown). In an example, the compressors 650 and 660 compress the processed gas to up to about 3600 psig to produce CNG or LNG which can then be delivered to a tanker trailer (not shown) or to a pipeline connection 670. The gas directed into the pipeline connection 670 can also be taken from storage tanks of a companion module or system 680 that is connected to the system 100 at a connection point 690, and that operates identically to the system 100 to produce the purified biogas.

The system 100 also includes a water supply system 500. The water supply system 500 includes a water reservoir 510 to which is attached a water makeup valve 535 to provide a source of water to replenish the amount of water lost through the normal operation of the system 100. A water pump 512 is disposed within the reservoir 510 and used to supply water to the piping 514 connecting the various components of the system 500. Additionally, while the system 500 does utilize the water makeup valve 535, the system 500 is designed as a closed loop system, thereby maximizing the utility of the water initially contained in the system 500. Further, the components of system 500, when arranged in proper sequence, afford maximum benefit of thermal exchanges utilizing the water contained in the system 500 to apply needed cooling of the compressors in system 300 and system 600 while providing beneficial heating of the water in the system 500 for optimum degasification, and for aiding other key process separations. This also minimizes additional energy consumption for waste heat removal and/or heat input, making the system 100 more efficient.

In a preferred embodiment of the system 100, when operated, the pump 512 initially drives water from the reservoir 510 into a heat exchange device 518 operably connected to a compressor cooling system 700. The system 700 is operably connected to the third compressor 650 that operates to compress the purified biogas prior to injection into the pipeline connection 670. Fluid contained within the system 700 is directed by a pump 702 through a chiller 704 to cool the fluid within the system 700. The cooled fluid then flows from the chiller 704 into a heat exchange device 706 that can be selectively operated through the use of a valve 710 to thermally contact the hydraulic operating fluid for the third compressor 650 with the cooled fluid from the chiller 704. When the valve 710 is opened, the hydraulic fluid passes through the device 706 to thermally contact, and be cooled by the cooled fluid from the chiller 704 to enable the third compressor 650 to be operated most effectively. From the device 706, the fluid passes through the heat exchange device 518 prior to re-entering the chiller 704 to thermally contact the water from the reservoir 510. Thus, the fluid in the system 700 also effectively provides a reduction in temperature for the water in the system 500. This cooling of the water to maintain an inlet temperature below 70 F provides enhanced gas absorption properties for the water within the scrubbing towers 411 and 412, consequently increasing the amount of biogas contaminants removed from the biogas by the water contacting the biogas in the towers 411 and 412.

From the device 518, the water is pressurized by a booster pump 525 and flows into one or more membrane separation devices 520 that effectively reduces the amount of certain components that have been absorbed by the water, such as any hydrogen sulfide, carbon dioxide, ammonia and in particular, nitrogen and oxygen. These biogas components tend to accumulate in the system 100 over time as the result of migration from the various devices that remove the components, thereby reducing the capacity of the water to absorb the biogas components from raw biogas. Because the system 500 operates to re-circulate the water within the system 500 for continuous usage, thereby utilizing a minimum quantity of water for water conservation purposes, properly cleaning the re-circulated water is imperative for making the system 500 a closed loop. Thus, the device 520 effectively removes these biogas components from the water to improve the absorption qualities of the water. In a particularly preferred embodiment, the device 520 is a passive flow through micro fiber contactor, such as a Liqui-Cel® membrane contactor from Membrana of Charlotte, N.C., which, when vacuum is applied, offers the benefit of simultaneous dissolved oxygen and nitrogen removal and all other necessary degassing with one step. It is necessary to filter any sediment from the water to five (5) micron levels before the water enters the device 520 to protect its integrity. In another embodiment, multiple devices 520 are employed in conjunction with an automated multiplexed filtration system 560 that can filter the water through one of multiple filtering devices 520 contained in the filtration system 560. The filtration system 560 allows continuous use and maintenance of the filter devices 520 in the filtration system when pressure drops increase as a result of filter loading by its capacity to direct the water flow via valves 535 through a previously unused filter device 520 within the filtration system 560 while the previously used device 520 is serviced or replaced.

After exiting the device 520, the water in the system 500 is directed by a pump 522 into the scrubbing towers 411 and 412 to effectively absorb and remove the carbon dioxide and other biogas contaminants from the natural gas in the manner described previously for the scrubbing system 400. When the water exits the second tower 411, the water is directed into the flash tank 413 where the methane absorbed by the water is reclaimed, at least in part.

Upon exiting the flash tank 413, the water can optionally be directed by valves 530 to the cooler 318 and/or a heat exchange device 532. The water directed to the cooler 318 thermally contacts the biogas stream from the pre-conditioner 314 and compressor 316 to effectively reduce the temperature of the biogas, while consequently increasing the temperature of the water. Further, either after or without passing through the cooler 318, the water enters the heat exchange device 532 that enables the water to thermally contact the hydraulic fluid used in operating the compressor 316. Again, this thermal contact effectively cools the hydraulic fluid, making the operation of the compressor 316 more effective, while increasing the temperature of the water.

After passing through one, both or neither of the cooler 318 and the heat exchange device 532, the heated water then is directed into a carbon dioxide stripper 540. The increased temperature of the water at 110-140 F entering the stripper 540 allows the absorbed gases in the water to be more effectively removed by the stripper 540, resulting in a cleaner recycled water flow. The water entering the stripper 540 is contacted in a counter-current fashion with an air flow from air source 545 that is pressurized by a compressor 555 prior to introduction into the stripper 540. The air flow removes the carbon dioxide and other contaminants from the water in a manner as is known in the art.

The water output from the stripper 540 is supplied to the reservoir 510, from which the water can be re-circulated through the scrubbing system 400 to clean additional volumes of biogas. With this construction, the water supply system 500 is self contained and operable with no external supply of water except for the small amounts of water introduced through the makeup valve 535' from a suitable water supply 570. A self-contained system 500 is advantageous, because it enables the gas processing system to operate regardless of the on-site water situation. Additionally, the water from the makeup water valve 535' is provided externally, but the majority of the water requirement for the water supply system 500 is met by re-circulated water.

In the system 500, the device 520 is specifically configured to remove oxygen and nitrogen from the water stream due to the increased concentrations of these contaminants that are present in the water stream as a result of the water passing through the stripper 540. As the stripper 540 is operated to remove the carbon dioxide absorbed from the biogas that is dissolved in the water, the operation of the stripper 540 results in increased amounts of oxygen and nitrogen being dissolved in the water exiting the stripper 540. The increase in the oxygen and nitrogen concentrations is due to the air flow directed through the stripper 540 to remove the carbon dioxide from the water. Essentially, a portion of the oxygen and nitrogen in the air replaces the dissolved carbon dioxide that is being removed from the water.

If left in the water, the elevated oxygen and nitrogen concentrations result in a reduction in the amount of carbon dioxide that can be absorbed by the water due to the presence of the oxygen and nitrogen. This, in turn, reduces the effectiveness of the water in being able to clean the biogas passing counter to the water within the scrubbing towers 411 and 412.

In addition, the elevated amounts of oxygen and nitrogen present in the water stream can be transferred from the water into the biogas stream within the scrubbing towers 411 and 412. Thus, instead of removing the oxygen and nitrogen contaminants, along with the carbon dioxide and other components, from the biogas stream, the water effectively adds to the amounts of these contaminants already present in the biogas. This, in turn results in processed biogas that has amount of oxygen and nitrogen present that exceed the specifications for compressed natural gas and pipeline quality natural gas, requiring that the gas be reprocessed. As a result, in addition to the benefit of creating the closed loop water supply system 500 to significantly reduce the water consumption of the overall system 100, the filtration members 520 also significantly reduce the levels of certain contaminants in the processed gas produced by the system 100 by removing these contaminants from the water in the system 500 prior to the water contacting the biogas.

In addition to the features of the system 100 discussed previously, one other significant aspect of the system 100 is the use of an automatic operating and monitoring system 800 to control the operation of the various components of the system 100. The system 800 includes a number of sensors 802 positioned on the various devices and components of the system 100 and operable to determine the particular operating parameters of the system 100. Each of the sensors 802 is operably connected via a suitable connection, e.g., wireless or hard wired line, to a controller 804 that receives the data from each of the sensors 802 for comparison with normal operational parameters stored within the controller concerning the operation of each portion of the system 100. The controller 804 is also operably connected via a suitable connection, e.g., wireless or hard wired line, to each of the operating controls (not shown) for the various components of each of the sub-systems 300, 400, 500, 600, and 700, as well as to an exterior communication network, such as the Internet 806 or a telephone line, in order to communicate the data received from the sensors 802 to a selected electronic device 808, such as a computer, PDA, telephone, or the like, monitored by a person supervising the operation of the system 100 from either a local or remote location. Thus, the system 100 can be operated and controlled by the system 800 in a manned or unmanned configuration.

Should one or more of the sensors 802 determine that there is a problem with or an out-of-spec parameter for the operation of a part of the system 100, the controller 804 is also directly operably connected to each of the components of the system 100 or their operating mechanism(s) (not shown) such that the controller 804 can act to alter the operation of the component, or to safely shut down the component and/or the overall system 100. In this circumstance, the controller 804 will also be able to alter the designated supervisor of the problem, such that the problem can be corrected and the system 100 returned to normal operation as soon as possible.

During normal operation of the system 100, the controller 804 is configured to be able to respond to changes in the outflow conditions of the processed gas from the scrubbing system 400. For example, because the output volume and pressure of the biogas from the digester 200 can vary during the day, the control system 800 will automatically adjust its operation to utilize the available biogas to maximize gas generating efficiency while protecting the digesters 200 and the associated boiler.

For example, the controller 804 employs a non-linear ramp logic to gradually increase system pressure based upon the number of digesters 200 available on startup for the system 100, as well as anytime the operating pressure of the system 100 is adjusted. This logic used in the controller 804 effects the demand rate made on the digesters 200 such that, based on digester pressure, the controller 804 can automatically adjust the operating set points for the system 100 to lower system demand during periods of low gas availability and raise system set points to take advantage of higher levels of gas availability.

In addition, the system 100 has many interdependent control loops (not shown) for each of the various sub-systems 300, 400, 500, 600 and 700 which can experience significant instability or oscillations during flow rate disturbances in any one or more of these systems. To account for and deal with these disturbances, the controller 804 includes adaptive logic which monitors the rate-of-change of process variables for each sub-system 300, 400, 500, 600 and 700 and their deviation from a predetermined set point to effectively modify the response for each sub-system 300, 400, 500, 600 and 700 to changing operating conditions. For example, in the water supply system 500, this logic can be implemented for monitoring the water level in the reservoir 510 and to monitor water pressure in the pipes connecting the various components of the water supply system 500. In a particularly preferred embodiment, the logic applies a calculated rate of change multiplier which is applied to the original IGain parameter that is determined during loop tuning for the water system 500 when the actual process variable rate-of-change exceeds the normal rate-of-change and the direction of change is away from the setpoint. The calculated rate of change multiplier is influenced by the amount of deviation from setpoint and the rate-of-change of the process variable: i.e. the greater the deviation, the greater the Maximum Rate-Of-Change Multiplier and the greater the rate-of-change, the greater the percentage of the Maximum Rate-Of-Change Multiplier applied to the original IGain parameter. The logic employed by the controller 804 is also selective as to when the modified response will be applied and the amount of response required response for each sub-system 300, 400, 500, 600 and 700.

Also, because the system 100 is configured to supply gas directly into a pipeline 670, the system 100 can potentially suffer significant downtime if there are many short term instances of off spec gas from the scrubber system 400 since the determination by the analyzer 620 in the final processing system 600 to cut off injection into the pipeline 670 must be made almost instantaneously to maintain the quality of the gas in the pipeline 670. As a result, the system 100 includes the accumulation tanks 640 to batch or mix, and store on spec gas prior to final compression and injection into the pipe line 670. The control logic utilized in the controller 840 employs a weighted averaging scheme during the filling of each of these tanks 640 which provides considerable tolerance during short periods when out of spec gas is detected by the gas analyzer 620. The mixing and storage of certain amounts of off spec gas with previously stored on spec gas in the tanks 640 enables the controller 840 to maintain continuous operations in the upstream sub-systems 300, 400, etc., while additionally maintaining acceptable pipe line quality for the gas stored in the tanks 640.

Furthermore, the water supply system 500 pumps against a head pressure as high as two hundred (200) psig during regular operation of the sub-system 500. If the water supply system 500 is shutdown for any reason, it can be extremely difficult to re-establish the water flow through the sub-system 500 as a result of this head pressure. To remedy this potential situation, the controller 840 is configured to incrementally reduce the head pressure in the water supply system 500. For example, when a restart of the water system 500 occurs and the pump 512 fails to establish flow within the water system 500 in a predefined amount of time, the water system 500 is shutdown and the flow of biogas is directed toward plant flare 1000 so as to lower the overall pressure in the system 100. The compressor 308 is also slowed to a minimum speed to help drop system pressure. When the system pressure drops 5 psig, as determined by one or more of the sensors 802, the controller 804 restarts and monitors the system 500 for flow establishment. If the flow is not established, this is sensed by the controller 804 and the entire process is repeated after another 5 psig drop in the overall system pressure. Once flow is established, the gas cleaning system 100 will return to normal operation by recharging the absorption columns 411, 412 with fresh biogas. Preferably, this function of the controller 804 is totally automatic, and does not require any operator intervention.

Also, during startup of the system 100, the water supply system 500 is brought online as soon as the available system pressure, e.g., a minimum system pressure of 50 psig and a minimum differential pressure across the valve 535" controlling the level of water in the reservoir 510 of 13 psig. Because this occurs at pressures well below the normal operating point for the water supply system 500, the large primary booster pump 512 is capable of overwhelming the flow capacity of the system 500 at start up, thus causing the water supply system 500 to have to shutdown due over-filled portions of the water supply system 500 and/or the biogas scrubbing system 400. The avoid this problem, the controller 804 is configured to gradually increase the water flow rate set point for the water supply system 500 as system pressure increased. Once the normal flow rate set point is achieved, the controller 804 can continuously monitor the flow rate to change the flow rate to accommodate varying pressure conditions in the water supply system 500.

The controller 804 also has the capability to record all of the operational data generated by the sensors 802, such as the quality of the gas being determined by the gas analyzer 620, and the volume of the gas stored in the tanks 640 and/or diverted into the pipeline connection 670. For example, the controller 804 can safely route any off spec gas from the system 400 to another acceptance path or to flare. The controller 840 can also perform weighted composition averaging of each quality criterion for all gas produced for stable production within specification, and if outflow gas is rejected by a receiving valve, disabled by a compressor fault, or the lack of a fresh receiving trailer, the controller 804 can determine or handle a safe routing for the gas or initiate a shutdown of the system 100, while recording and reporting all events that caused the shut down.

While the system 800 also includes fully operational controls and informational instrumentation at the site of the system 100, the system 800 also allows for the system to be completely started, operated and shutdown remotely. In addition, an emergency power backup system 900 is connected to the system 800 to power the system 800 including the sensors 802 and the controller 804 to maintain supervisory control of the entire system 100 for safe shutdown when electrical power fails.

Various other embodiments of the present invention are contemplated as being within the scope of the following claims particularly pointing and distinctly claiming the subject matter regarded as the invention.

We claim:

1. A biogas system comprising:
   a) a first compressor having a biogas input and a compressed biogas output;
   b) a first pump having a water pump input and a water pump output;
   c) a first scrubber tower having a first mixing chamber, a first compressed gas input, a first water input connectable to the water pump output of the first pump, a first water output, and a first processed gas output, the first mixing chamber in communication with the first compressed gas input, the first processed gas output, the first water input and the first water output; and
   d) a water filtration member operably connected to the first water output, the filtration member configured to remove contaminants from the water exiting the first scrubber tower wherein the water filtration member is configured to remove oxygen from the water entering the water input of the first scrubber tower.

2. A biogas processing system comprising:
   a) a first compressor having a biogas input and a compressed biogas output;
   b) a first pump having a water pump input and a water pump output;
   c) a first scrubber tower having a first mixing chamber, a first compressed gas input, a first water input connectable to the water pump output of the first pump, a first water output, and a first processed gas output, the first mixing chamber in communication with the first compressed gas input, the first processed gas output, the first water input and the first water output; and
   d) a water filtration member operably connected to the first water output, the filtration member configured to remove contaminants from the water exiting the first scrubber tower wherein the water filtration member is a membrane contactor.

3. The biogas processing system of claim 2 further comprising a hydrogen sulfide removal device operably connected to the biogas input of the first compressor.

4. The biogas processing system of claim 2 further comprising a moisture separator device operably connected to the biogas input of the first compressor.

5. The biogas processing system of claim 2, further comprising a cooling device operably connected to and upstream of the first water input.

6. The biogas processing system of claim 2 further comprising a controller operably connected to the first compressor, the first pump, the first scrubber tower, and the water filtration member, the controller configured to adjust the operating parameters of at least one of the first compressor, the first pump, and the first scrubber tower in response to changes in a biogas flow connected to the biogas input of the first compressor.

7. The biogas processing system of claim 6 wherein the controller is configured to adjust the operating parameters of the first pump in response to changes in a flow of water through the first pump.

8. The biogas processing system of claim 7 wherein the change in the flow of water through the first pump occurs during start up of the biogas processing system.

9. The biogas processing system of claim 2 wherein water flowing through the first pump, first scrubber tower and water filtration member is maintained at a temperature of below 140° F.

10. A biogas processing system comprising:
    a) a first compressor having a biogas input and a compressed biogas output;
    b) a first pump having a water pump input and a water pump output;
    c) a first scrubber tower having a first mixing chamber, a first compressed gas input, a first water input connectable to the water pump output of the first pump, a first water output, and a first processed gas output, the first mixing chamber in communication with the first compressed gas input, the first processed gas output, the first water input and the first water output; and
    d) a water filtration member operably connected to the first water output, the filtration member configured to remove contaminants from the water exiting the first scrubber tower wherein the water filtration member is configured to remove nitrogen from the water entering the water input of the first scrubber tower.

11. A method of processing a biogas, the method comprising:
    a) providing a biogas processing system comprising a first compressor having a biogas input and a compressed biogas output, a first pump having a water pump input and a water pump output, a first scrubber tower having a mixing chamber, a compressed gas input, a water input connectable to the water pump output of the first pump, a water output, and a processed gas output, the mixing chamber in communication with the compressed gas input, the processed gas output, the water input and the water output, and a water filtration member operably connected to the water output of the first scrubber tower, the filtration member configured to remove contaminants from the water exiting the first scrubber tower, wherein the water filtration member is a membrane contactor;
    b) directing a flow of water from the first pump through the filtration member to filter the flow of water;
    c) directing a flow of biogas from the first compressor into the compressed gas input of the first scrubber tower;
    d) directing the flow of water from the filtration member into the water input of the first scrubber tower to contact the flow of biogas; and
    e) directing the flow of water from the water output of the first scrubber tower to the first pump.

12. The method of claim 11 wherein the biogas processing system further comprises a cooling device operably connected to and upstream of the water input of the first scrubber tower, the method further comprising the step of directing the flow of water through the cooling device prior to directing the flow of water to the filtration member from the first pump.

13. The method of claim 11 wherein the steps of directing a flow of water from the first pump through the filtration member to filter the flow of water, directing the flow of water from the filtration member device into the water input of the first scrubber tower to contact the flow of biogas and directing the flow of water from the water output of the first scrubber tower to the first pump are performed within a closed loop water recirculation system.

14. The method of claim 11 wherein the biogas processing system further comprising a controller operably connected to at least one of the first compressor, the first pump, the first scrubber tower, and the water filtration member, the controller configured to adjust the operating parameters of at least one of the first compressor, the first pump, and the first scrubber tower in response to changes in a biogas flow connected to the biogas input of the first compressor, and wherein the method further comprises the step of adjusting the operating parameters of at least one of the first compressor, the first pump, and the first scrubber tower in response to changes in a biogas flow connected to the biogas input of the first compressor prior to directing a flow of water from the first pump through the filtration member to filter the flow of water.

15. The method of claim 14 wherein the step of adjusting the operating parameters comprises adjusting the operating parameters of the first pump in response to changes in a flow of water through the first pump.

16. The method of claim 15 wherein the step of adjusting the operating parameters of the first pump comprises adjusting the flow of water through the first pump during start up of the biogas processing system.

17. The method of claim 12 wherein the step of directing the flow of water through the cooling device cools the flow of water to a temperature of below 140° F.

18. A method of processing a biogas, the method comprising:
a) providing a biogas processing system comprising a first compressor having a biogas input and a compressed biogas output, a first pump having a water pump input and a water pump output, a first scrubber tower having a mixing chamber, a compressed gas input, a water input connectable to the water pump output of the first pump, a water output, and a processed gas output, the mixing chamber in communication with the compressed gas input, the processed gas output, the water input and the water output, and a water filtration member operably connected to the water output of the first scrubber tower, the filtration member configured to remove contaminants from the water exiting the first scrubber tower;
b) directing a flow of water from the first pump through the filtration member to filter the flow of water;
c) directing a flow of biogas from the first compressor into the compressed gas input of the first scrubber tower;
d) directing the flow of water from the filtration member into the water input of the first scrubber tower to contact the flow of biogas; and
e) directing the flow of water from the water output of the first scrubber tower to the first pump wherein the filtration member is configured to remove oxygen, and wherein the step of directing the flow of water through the filtration member to filter the flow of water comprises filtering dissolved oxygen from the flow of water.

* * * * *